United States Patent
Banisakher et al.

(10) Patent No.: US 11,537,888 B2
(45) Date of Patent: Dec. 27, 2022

(54) SYSTEMS AND METHODS FOR PREDICTING PAIN LEVEL

(71) Applicants: Deya Banisakher, Miami, FL (US); Naphtali Rishe, Miami Beach, FL (US); Mark Finlayson, North Bay Village, FL (US)

(72) Inventors: Deya Banisakher, Miami, FL (US); Naphtali Rishe, Miami Beach, FL (US); Mark Finlayson, North Bay Village, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 16/875,041

(22) Filed: May 15, 2020

(65) Prior Publication Data
US 2020/0364566 A1 Nov. 19, 2020

Related U.S. Application Data

(60) Provisional application No. 62/848,179, filed on May 15, 2019.

(51) Int. Cl.
*G06N 3/08* (2006.01)
*G06N 3/04* (2006.01)
*G16H 70/60* (2018.01)
*G16H 50/20* (2018.01)
*G16H 10/60* (2018.01)

(52) U.S. Cl.
CPC ............ *G06N 3/08* (2013.01); *G06N 3/0445* (2013.01); *G16H 50/20* (2018.01); *G16H 70/60* (2018.01); *G16H 10/60* (2018.01)

(58) Field of Classification Search
CPC ........ G06N 3/08; G06N 3/0445; G16H 70/60; G16H 50/20; G16H 10/60
See application file for complete search history.

(56) References Cited

U.S. PATENT DOCUMENTS

| | | | |
|---|---|---|---|
| 2008/0033658 A1* | 2/2008 | Dalton | G16H 10/20 702/19 |
| 2011/0172501 A1* | 7/2011 | Antonijevic | C12Q 1/6883 600/300 |
| 2020/0342352 A1* | 10/2020 | Neumann | G16H 20/70 |

OTHER PUBLICATIONS

Kachele, Markus, et al. "Adaptive confidence learning for the personalization of pain intensity estimation systems." Evolving Systems 8.1 (2017): 71-83. (Year: 2017).*
Deya M. Banisakher, Naphtali Rishe, Mark A. Finlayson, Ivanka Marinovic. "A Supervised Classification Approach to Predicting Knee Pain Improvement in Osteoarthritis Patients." Proceedings of the 30th International FLAIRS Conference. Marco Island, Florida. May 22-24, 2017. (Year: 2017).*
Godbole, Shantanu, and Sunita Sarawagi. "Discriminative methods for multi-labeled classification." Pacific-Asia conference on knowledge discovery and data mining. Springer, Berlin, Heidelberg, 2004. (Year: 2004).*
Liu, Bing, et al. "Building text classifiers using positive and unlabeled examples." Third IEEE International Conference on Data Mining. IEEE, 2003. (Year: 2003).*
Lipton, Z. Chase, Charles Elkan, and Balakrishnan Narayanaswamy. "Thresholding classifiers to maximize f1 score." arXiv preprint ArXiv:1402.1892 14 (2014). (Year: 2014).*
Ketabdar, Hamed, Jonas Richiardi, and Andrzej Drygajlo. "Global feature selection for on-line signature verification." Proceedings International Graphonomics Society 2005 Conference. 2005. (Year: 2005).*
Ali, Peshawa Jamal Muhammad, et al. "Data normalization and standardization: a technical report." Mach Learn Tech Rep 1.1 (2014): 1-6. (Year: 2014).*

* cited by examiner

*Primary Examiner* — Li B. Zhen
*Assistant Examiner* — Henry Nguyen
(74) *Attorney, Agent, or Firm* — Saliwanchik, Lloyd & Eisenschenk

(57) ABSTRACT

Devices and methods for learning and/or predicting the self-reported pain improvement levels of osteoarthritis (OA) patients are provided. A device or apparatus can include a processor and a machine-readable medium in operable communication with the processor and having stored thereon an algorithm and a unique set of features. The algorithm and set of features can enable building one or more models that learn the self-reported pain improvement levels of OA patients.

5 Claims, No Drawings

SYSTEMS AND METHODS FOR PREDICTING PAIN LEVEL

CROSS-REFERENCE TO A RELATED APPLICATION

This application claims the benefit of U.S. Provisional Application Ser. No. 62/848,179, filed May 15, 2019, which is hereby incorporated by reference herein in its entirety, including any figures, tables, and drawings.

BACKGROUND

Knee osteoarthritis (OA) is the most common joint illness in adults around the world. Previous research has demonstrated that the early analysis and treatment of knee OA could counteract development of symptoms. Thus, clinicians are faced with the challenge of recognizing patients who are at high risk of radiographic and symptomatic knee OA and projecting their treatment outcomes in an opportune and proper way.

The National Institute of Health (NIH) describes some of the common features of people at high risk for OA generally: females over 45 years of age; overweight people; and people "with jobs that stress particular joints". To assess the connection between those features and knee OA specifically, a few strategies have been proposed in the past. Screening surveys for symptomatic knee OA have been used in view of patients' self-reported side effects. Nonetheless, such screening methods demonstrate low specificity, and cannot predict radiographic knee OA without associated pain.

BRIEF SUMMARY

Embodiments of the subject invention provide novel and advantageous devices and methods for learning and/or predicting the (self-reported) pain improvement levels of osteoarthritis (OA) patients (e.g., knee OA patients). A device or apparatus can include a processor and a machine-readable medium (e.g., a (non-transitory) computer-readable medium) in operable communication with the processor and having stored thereon an algorithm and a unique set of features (see, e.g., Table 2 herein). The algorithm and/or set of features can be embodied as a set of instructions stored on the machine-readable medium that, when executed by the processor, perform steps (including steps of the algorithm). The algorithm and set of features can enable building one or more models that learn the (self-reported) pain improvement levels of OA patients (e.g., knee OA patients).

In an embodiment, a system for predicting a pain level of an OA patient can comprise: a processor; and a machine-readable medium in operable communication with the processor and having instructions stored thereon that, when executed by the processor, perform the following steps: developing a set of classifiers, the set of classifiers comprising three classifiers corresponding to a first category, a second category, and a third category, respectively; training the set of classifiers; testing the set of classifiers; and using the set of classifiers to predict the pain level of the OA patient at a future visit intended to assess the pain level. The first category can be that pain has improved for the OA patient since a previous visit; the second category can be that pain has remained unchanged for the OA patient since the previous visit; and the third category can be that pain has worsened for the OA patient since the previous visit. The developing, training, testing, and using of the set of classifiers can comprise using a machine learning (ML) technique, such as an eminent support vector machine (SVM), a random decision forest (RDF), a backpropagation neural network, or a recurrent neural network (RNN). The training of the set of classifiers can comprise training the set of classifiers using a dataset with known values and/or the testing of the set of classifiers comprising testing the set of classifiers using the dataset with known values. The dataset can be broken into a first sub-dataset to be used for the training of the set of classifiers and a second sub-dataset to be used for the testing of the set of classifiers. The developing of the set of classifiers can comprise feature selection, and the training of the set of classifiers comprising normalization of data obtained from a dataset with known values used to train the set of classifiers. The using of the set of classifiers to predict the pain level of the OA patient can comprise using the set of classifiers to predict the pain level of the OA patient at an Nth visit based on features of the set of classifiers reported on all visits up to an (N−1)th visit. The dataset with known values can, for example, the Osteoarthritis Initiative (OAI) dataset.

In another embodiment, a method for predicting a pain level of an OA patient can comprise: developing (e.g., by a processor) a set of classifiers, the set of classifiers comprising three classifiers corresponding to a first category, a second category, and a third category, respectively; training (e.g., by the processor) the set of classifiers; testing (e.g., by the processor) the set of classifiers; and using (e.g., by the processor) the set of classifiers to predict the pain level of the OA patient at a future visit intended to assess the pain level. The first category can be that pain has improved for the OA patient since a previous visit; the second category can be that pain has remained unchanged for the OA patient since the previous visit; and the third category can be that pain has worsened for the OA patient since the previous visit. The developing, training, testing, and using of the set of classifiers can comprise using an ML technique, such as an eminent SVM, an RDF, a backpropagation neural network, or an RNN. The training of the set of classifiers can comprise training the set of classifiers using a dataset with known values and/or the testing of the set of classifiers comprising testing the set of classifiers using the dataset with known values. The dataset can be broken into a first sub-dataset to be used for the training of the set of classifiers and a second sub-dataset to be used for the testing of the set of classifiers. The developing of the set of classifiers can comprise feature selection, and the training of the set of classifiers comprising normalization of data obtained from a dataset with known values used to train the set of classifiers. The using of the set of classifiers to predict the pain level of the OA patient can comprise using the set of classifiers to predict the pain level of the OA patient at an Nth visit based on features of the set of classifiers reported on all visits up to an (N−1)th visit. The dataset with known values can, for example, the OAI dataset.

DETAILED DESCRIPTION

Embodiments of the subject invention include novel and advantageous devices and methods for learning and/or predicting the (self-reported) pain improvement levels of osteoarthritis (OA) patients (e.g., knee OA patients). A device or apparatus can include a processor and a machine-readable medium (e.g., a (non-transitory) computer-readable medium) in operable communication with the processor and having stored thereon an algorithm and a unique set of features (see, e.g., Table 2 herein). The algorithm and/or set of features can be embodied as a set of instructions stored on the machine-readable medium that, when executed by the processor, perform steps (including steps of the algorithm). The algorithm and set of features can enable building one or more models that learn the (self-reported) pain improvement levels of OA patients (e.g., knee OA patients).

In related art devices and methods, patients must physically visit their medical providers regularly to have an assessment of their OA status and to report their pain levels at the time of the visit. This process involves physical tests, imaging, and demonstrative activities that the patients are asked to perform, such as chair sits and stands and short distance walks. The pain level obtained is self-reported by patients, typically using an outcome scoring system such as the Knee Osteoarthritis Outcome Score (KOOS) and/or the Western Ontario and McMaster Universities Osteoarthritis Index (WOMAC). Embodiments of the subject invention can predict the change in KOOS score for a patient's future visit using previously measured indicators or features (i.e., from a previous visit). The algorithm outputs a classification in one of three categories (improved, unchanged, worsened) corresponding to the predicted future pain level.

The algorithm can rely on an ensemble machine learning approach, such as a Recurrent Neural Network (RNN). The algorithm can include developing, training, and testing a set of three RNN classifiers, each corresponding to one of three categories (improved, unchanged, worsened). In an embodiment, the algorithm can be trained to predict the reported pain of patients over a span of time of up to nine years. Three single-class multi-label RNN classifiers can be elaborated, where a patient is classified into one of the aforementioned categories. A total of nine labels can be used, corresponding to the patients' self-reported pain levels during the nine annual visits. For each label, the classifiers incorporate the feature values recorded at the time point of the respective label. Hence, to learn or predict the pain level at the $N^{th}$ visit, only features reported up to the $(N-1)^{th}$ visit are used.

In an embodiment, in order to produce a complete prediction of the pain category progress for the OA patients, an ensemble step of the classifiers corresponding to the three classes (improved, unchanged, and worsened) can be used. This is necessary because the three classifiers in each method are independent and only show one dimension (each) of the prediction result. Final combined prediction results per algorithm, for an example test, are shown in Table 6 herein.

In many embodiments, the algorithm performing the combined predictions can be summarized as follows: for each of the nine labels, the algorithm examines the outputs of each of the three classifiers and takes a weighted vote to determine whether a patient's pain level has been improved, unchanged, or worsened with respect to the previous reporting. There are eight possible scenarios in play, with four distinct cases outlined below:

1. All three classifiers predict a positive class (that is, improved, unchanged, and worsened): the algorithm here chooses the classifier with the highest F1-score as the prediction for that label.
2. All three classifiers predict a negative class (that is, not improved, not unchanged, and not worsened): the entire data point (i.e., the patient) is marked as a miss. The algorithm halts for that patient and does not compute any further predictions for the rest of the labels.
3. Two of the classifiers predict a negative class, while the other predicts a positive result. The classifier with the positive result is chosen to vote.
4. Two of the classifiers predict a positive class while a negative class is predicted by the third: in this case, the classifier with the highest F1-score is chosen to vote. Here there are two subcases: first, if the classifier with the highest F1-score predicts a positive class, its prediction is simply chosen. Second, if it predicts a negative class, the second-best performing classifier that predicts a positive class is taken.

In an embodiment, the publicly available Osteoarthritis Initiative (OAI) dataset can be used to extract features and to train and test the models. The datasets can be split into two major sets (training set and testing set) in order to evaluate the model over unseen data points. The RNN model of embodiments of the subject invention was evaluated against the OAI dataset and compared to three other machine learning models that were also built. The RNN model achieved an average F1-measure of 0.81 (81%) on the test set (see Table 6 herein). This embodiment should not be construed as limiting.

By utilizing embodiments of the subject invention, projection of pain outcomes related to OA (e.g., knee OA) can be improved by an apparatus leveraging existing large databases of patient data and machine learning techniques. The apparatuses, devices, and methods of embodiments of the subject invention can apply machine learning models using, for example, RNNs to predict the self-reported pain improvement of OA patients (e.g., knee OA patients).

Machine learning (ML) approaches to OA diagnosis and pain predication is relatively unexplored in the related art, but embodiments of the subject invention can use ML to help distinguish patients' pain outcome trajectories and improvement given certain treatments. Embodiments show that projection of pain outcomes related to knee OA can be improved by leveraging existing large databases of patient data and ML techniques. The feasibility of predicting an OA patient's pain improvement or trajectory over nine years based on a given set of features has been demonstrated. Several ML techniques and algorithms can be used, including the eminent Support Vector Machine (SVM), Random Decision Forest (RDF), and variations of Artificial Neural Network (ANN) algorithms. The methods leveraged for this task consider the differences in patients' sex, age, body mass index (BMI), injury factors, and occupation factors. In addition, the models developed involve calculation of several features that further include physical and clinical examination of the patient, including the recorded physical activity and other self-reported variables.

Most studies utilizing ML models for OA-related tasks have focused on image classification. There have been a few attempts to apply ML to OA-risk identification. These works focused on Logistic Regression (LR) analysis methods and variants thereof, and they have been widely used for various prediction and classification tasks related to OA monitoring and diagnosis such as predicting outcomes after surgery, risk and pain analysis, as well as classifying patients as OA patients from others. These statistical analysis methods proved successful in some cases. However, in most cases, these are methods that require extensive formal statistical training, making them far from ideal in a clinical practice. These methods further proved to be time consuming due to the involvement many variants and entities that could not be merged to give a clear result in some cases. LR prediction models involved calculation of LR equations based on factors such as age, gender and BMI of an individual. Reports were developed through assessment of clinical data, physical examination and blood sample for genetic follow up.

Researchers have also attempted to build descriptive models of OA patients based on reported pain. However, most were focused on the identification of subgroups of patients rather than the long-term prediction of pain. These studies have examined hip OA, knee OA, and combinations of both. The methods used for the former studies have mainly been variations of two-step cluster analysis or latent class growth modeling. Although some of the studies were successful in identifying patient subgroups based on pain trajectories for two to six years, their models were selective in terms of patient population, limited in time (as most used data spanning for less than 5 years), and in some cases, ineffective or ungeneralizable when faced with a new population of patients.

The process of building, training, and testing 12 ML models using four ML algorithms will be described below.

Methodology

The Dataset

The data used in the preparation of the examples were obtained from the OAI dataset, which is available for public access at http://www.oai.ucsf.edu. Specific datasets used along with their respective version numbers are listed in Table 1. The dataset's cohort consists of an ethnically diverse group of women and men ages 45 to 79 equally distributed along each age/gender group. Participants were followed for over nine years for changes in the clinical status of their respective OA conditions including worsening, improvement, and onset of symptoms and disabilities. This was achieved by assessing the patients physically using traditional methods at the participating clinics in an annual manner. Information collected included biomarkers, joint symptoms, general health and function, medication history and inventory, and physical exam measurements. In total, there were 4,796 patients enrolled for the baseline visit, which shrunk to 3,444 for the last recorded annual visit ($108^{th}$ month).

The focus of the OAI dataset is on knee OA. Per the OAI website, "the overall aim of the OAI is to develop a public domain research resource to facilitate the scientific evaluation of biomarkers for osteoarthritis as potential surrogate endpoints for disease onset and progression". Two of the OAI dataset objectives are to provide data for the purposes of scientific evaluation of biomarkers for OA, and to support the study of the natural history of knee OA onset and progression as well as the progression of risk factors associated with knee OA. Embodiments of the subject invention also address these two objectives.

Overall Approach

In many embodiments, the major steps of the approach are as listed below, starting with the OAI dataset as input and resulting in an output of labels corresponding to pain categories that can be assessed:

1) Data preprocessing—formatting and cleaning;
2) Feature selection and representation;
3) Label preparation and representation; and
4) Classification—model training and testing.

TABLE 1

OAI datasets used and corresponding versions†.

| Dataset | Release Version |
| --- | --- |
| Baseline AllClinical | 0.2.2 |
| 12-month AllClinical | 1.2.1 |
| 18-month AllClinical | 2.2.2 |
| 24-month AllClinical | 3.2.1 |
| 36-month AllClinical | 5.2.1 |
| 48-month AllClinical | 6.2.2 |
| 60-month AllClinical | 7.2.1 |

TABLE 1-continued

OAI datasets used and corresponding versions†.

| Dataset | Release Version |
| --- | --- |
| 72-month AllClinical | 8.2.1 |
| 84-month AllClinical | 9.2.1 |
| 96-month AllClinical | 10.2.2 |
| 108-month AllClinical | 11.2.1 |

Data Preprocessing

Data preprocessing methods can include two steps: formatting; and cleaning. In formatting, the data obtained from OAI can be extracted from its original ASCII format into a relational database to ease programmatic access and manipulation. In cleaning, 1,862 incomplete records (i.e., records with missing data) were removed. Also, an additional 396 randomly selected records were removed to ensure a similar gender (53% female and 48% male) and age distribution to the original dataset. This resulted in 2,538 records (out of 4,796 records originally) used for the remainder of the process.

Feature Selection and Representation

The OAI dataset is composed of three major types of data: categorical variables; continuous variables; and imaging-related variables. In many embodiments, only categorical and continuous variables are considered. The features selection procedure can eliminate many of these features from consideration, as described below.

Feature selection was split into two tasks: first, individual feature selection, in which 100 features were selected by hand; and second, automatic feature extraction, which used statistical methods to further reduce the number of features used.

For individual feature selection, a set of 100 features extracted from 73 variables were identified and a simple combination of features mentioned. This included demographic features such as age, gender, race, and ethnicity, in addition to features regarding the patients' medical history, strength measures, and physical activity and its respective performance measures.

In order to identify the features with the most discriminative power, two statistical measures were taken at first: the Fisher coefficient; and the squared Euclidean distance. The Fisher coefficient represents the ratio between class-variance to within-class variance, while the squared Euclidean distance is a widely-used class distance measure. Both methods are commonly used for the identification of discriminant features. Next, a ranking of the features was generated based on the methods' criteria.

Four major data representation techniques were applied to better represent the features. Although presented in order, the following methods are independent from each other. First, the continuous age and BMI, were rescaled to a unified range between 0 and 1. This is especially necessary when variables or features have widely different scales. For example, the feature age has a real value between 45 and 79 in OAI while the feature gender is either 0 or 1. If the data is not scaled in this case, the age feature will overtake the gender feature in terms of importance due to scaling issues and not because it is more or less significant. Rescaling is also called normalization. Second, certain features were decomposed into their independent constituents. For example, the feature 20-meter walk—where the patients were asked to walk 20 meters (m) while the number of steps and the time taken to complete the task were recorded—into the features 20-meter walk number of steps and the feature 20-meter walk time to complete. Third, some features were aggregated to produce more meaningful features and reduce the feature space. The features Hip_arthritis, back_arthritis and hand_arthritis were combined into a single feature called other_arthritis. Other aggregated features were past_medication and arth_injections. Fourth, all features were binarized; that is, they were transformed using a binary threshold function where feature values are either 1 when higher than the threshold and 0 when lower. Finally, a descriptive list of the features used for the models developed is shown in Table 2.

Label Preparation and Representation

The OAI datasets include self-reported pain levels of the patients. This was collected using the KOOS questionnaire, including all its subscales. OAI patients were presented this questionnaire at the baseline visit, as well as at the following nine annual visits. This data was used as the basis for the pain label calculation. Starting from the $12^{th}$ month visit, labels per patient per visit were generated as improved, unchanged, and worsened. These labels were calculated by comparing the self-reported pain values at the current visit with respect to the previous visit. The label vectors were binarized with respect the three categories/labels created to serve the single-class classifiers. The result is a label vector per record (patient) for each of the three categories of length 9 representing the follow-up visits where each value is a 0 or 1 with respect to its category, that is improved or not, unchanged or not, worsened or not.

Data Preparation for Training and Testing

The first stage of classification is model training, followed by a stage of model validation (namely, cross-validation), and finally a stage of testing on a separate (unseen) set. The original data was split into two main sets, 80% in a training set and 20% in testing set (2,030 and 508 records, respectively).

TABLE 2

List of main features and their decomposed and sub-features (used in model training and testing)

| Parent Feature | Sub-features | Rank |
|---|---|---|
| age | 45-49 | 2 |
| | 50-54 | |
| | 55-59 | |
| | 60-64 | |
| | 65-69 | |
| | 70-74 | |
| | 75-79 | |
| gender | male | 4 |
| | female | |
| BMI | underweight | 5 |
| | normal | |
| | overweight | |
| | obese class I | |
| | obese class II | |
| | obese class III | |
| Performance measures | 20-meter walk: pace (m/sec) | 3 |
| | Single chair stand | 3 |
| | Repeated chair stands: able to complete 5 stands | 9 |
| | Repeated chair stand: pace in stands/sec | 10 |
| physical activity | Kneel 30 minutes or more during single day, past 30 days | 11 |
| | Get in and out of squatting position 10 or more times during single day, past 30 days | 12 |
| | Squat 30 minutes or more during single day, past 30 days | 13 |
| | flight of stairs completed, past 7 days | 15 |
| | Climb up a total of 10 or more flights of stairs during single day, past 30 days | 14 |
| | Lift or move objects weighing 25 pounds or more by hand during single day, past 30 days | 17 |
| Medical History | RA/other inflammatory arthritis diagnosis | 1 |
| | pain medication use, past 30 days | 6 |
| | injections for treatment of arthritis, past 6 months | 7 |
| | Fallen and landed on floor or ground, past 12 months | 8 |
| | Past pregnancy | 16 |

Following is a brief description of each of the four ML models adapted for these examples.

Support Vector Machine

Support vector machines (SVMs) are supervised ML models widely used for data analysis regression and classification applications. One of the advantages of SVMs is that they are capable of both linear and non-linear classification of data. This mechanism works in a way whereby data entered is placed categorically to certain classes that are closely associated. The model's performance is measured by the systems capability to predict results using the data presented.

Three single-class multi-label SVM classifiers were developed where each patient was classified as one of the following categories: improved; unchanged; or worsened experienced knee pain. A total of nine labels were used corresponding to the patients' self-reported pain levels during the nine annual visits. For each label, the classifiers incorporated the feature values recorded at the time point of the respective label. For example, to learn or predict the pain level at the $N^{th}$ visit, only features reported up to the $N-1^{th}$ visit were used. Because it was not possible to have a value for the change in pain level at the baseline visit, three new categories were created to aid in the prediction of the first annual visit, i.e., the first label representing the $12^{th}$ month visit: high; low; and medium pain. These acted as values for the previous year pain level feature discussed earlier.

Random Decision Forest

Random Decision Forests (RDFs) are ensemble learning methods and are employed in regression and classification applications. They operate through the construction of numerous decision trees during the training stage. The technique outputs the class that contains the mode of the classes of the collection of collection of tress. This technique is very influential especially in data mining applications. A major advantage RDF has over regular decision tress is that the former method avoids overfitting the training set unlike the latter. Overfitting is the portrayal of random error and noise by a statistical model instead of an underlying pattern. This occurs in complex models where a small number of examples are presented in relation to the feature space. An overfitted model results in poor prediction performance and can be sensitive to minor variations in the training set.

A similar setup to that of the SVM models was employed here. Three single-class multi-label RDF classifiers were built based on the same pain categories discussed earlier. The label space is also identical to that used in the SVM model.

Backpropagation Neural Network

Backpropagation Neural Network is another supervised ML scheme. Backpropagation, alternatively referred to as backward propagation of errors, is one of the methods used to train ANNs. The method works hand in hand with various optimization techniques in a two-phased cycle—propagation and weight update. The technique works by comparing a newly entered data's output with the existing data, then performing an error approximation where all the initially entered data are accredited with the errors equally. The error can be propagated backwardly to approximate the associated contribution of error to the original output.

The same structure was followed for neural network as in the previous two models, where three single-class multi-label classifiers were built for the pain categories: improved; unchanged; and worsened. Some effective variations of this algorithm can be used. First, an adaptive learning rate was used in order to avoid oscillation of weights and to improve the convergence rate at which the network outputs a prediction. Second, an inertia or momentum variable was integrated, which aids in the overall performance of the model during training and improves the learning speed during training. Third, the Nguyen-Widrow layer initialization function was employed, which is attributed with drastically decreasing the training time.

Recurrent Neural Network

Recurrent Neural Networks (RNNs) are yet another type of ANN. They also utilize the principle of backpropagation of errors with a slight twist—this is called backpropagation through time. RNNs are commonly used in speech and text recognition as they are famed for handling an arbitrary sequence of inputs and outputs. RNNs have also been used in multiple other applications including model prediction. The main difference between RNNs and other ANNs is the internal layer cycling in RNNs, which allows them to perform well with sequential data. The Long Short Term Memory variant of RNNs was used. This algorithm alleviates the gradient vanish issue with RNNs. Finally, the architecture discussed in the previous models was followed here as well. Three more classifiers were built, and they were single-class multi-label coupled with the same structure and processing for the class and label spaces. Therefore, a total of 12 individual classifiers were developed for this task, which later were combined in an ensemble fashion to give a single result for each patient at each of the 9 follow-up visits.

Model Training and Validation

The SVM classifiers were trained using the RBF kernel function and a soft margin C of 10,000—a common setup. For the RDF classifiers, a slightly larger number of parameters to optimize exists. The max_features parameter was set to the square root of the total number of features in an individual run, the number_of_trees parameter was set arbitrarily to 100, where this is referring to the number of trees to be built before taking the average of votes for predictions. Additionally, the min_sample_leaf parameter was set to 50. As for the backpropagation ANNs, all weight initialization was done using the Nguyen-Widrow layer initialization function, where the weights are assigned small random values. The bias parameters were all set to small non-negative values initially. Further, the adaptive learning rate was set to 0.01 for the improved-class classifiers, and to 0.1 for the unchanged and worsened-class classifiers. The momentum value was set to 0.1 for all three classifiers. The sigmoid function was used for training. The binary_crossentropy loss function was used, and Adam's optimization algorithm was followed. The algorithm showed the optimal parameter values to be 5 for the number of epochs and 26 for the batch size.

Tools Employed

Several tools were used to implement the underlying processes outlined above. For the relational database built during data preprocessing, PostgreSQL was used. Data analysis was performed using Java and R, as was training and testing of the models. Table 3 contains a list of the publicly available packages and libraries that were used for the training and testing.

Results

Model Validation

The training set was used for the training as well as for the validation stages. All 12 individual classifiers were trained separately on the training set, and later validated using a 10-fold cross-validation method. All the parameter selection and tuning was performed with the aid of grid search. Grid search, also called parameter sweep, is the traditional method used for hyperparameter optimization that performs exhaustive searching over a predefined hyperparameter space for a specified learning algorithm. Cross-validation was performed on the training set as a performance measure for the hyperparameter optimization and to prevent overfitting by the SVM and the ANN classifiers. The average cross-validation results per classifier are presented in Table 4. All results are presented using the F-measure (also referred to as $F_1$-score), which considers the harmonic average of precision and recall to compute the final score between 0 and 1, where 1 is a perfect score.

Model Testing

The 12 classifiers were tested over the testing set only, which was not introduced to the models previously. All testing was done in a similar fashion. After the classifiers were presented with the test data, their generated outputs were compared against the true label values, which accounted for a hit or miss. The performance metric used for evaluation is the $F_1$-score. Additionally, for comparison, a baseline metric was calculated using the popular Most Frequent Class technique (MFC). Table 5 shows the testing results for all 12 classifiers per label (the labels are indexed by visit number, where Visit 1 corresponds to the $12^{th}$ month visit, while the rest of the visits follow annually). The average column shows the average $F_1$-scores for the corresponding classifiers.

TABLE 3

Software libraries and packages used.

| Language | Library | Modules |
|---|---|---|
| Java | Java-ML[31] | SVM |
| R-CRAN distribution | rpart[32] | RDF |
| | e1071[33] | Cross-validation |
| | PARTY[34] | RDF |
| | CARET[35] | Cross-validation |
| | kernLab[36] | SVM |
| | randomForest[37] | RDF |
| | nnet[38] | ANN (Backprob) |
| | rnn[39] | RNN |

TABLE 4

Average cross-validation results during the training phase.

| Algorithm | Classifier | Average ($F_1$) |
|---|---|---|
| SVM | improved | 0.553 |
| | unchanged | 0.631 |
| | worsened | 0.627 |
| RDF | improved | 0.733 |
| | unchanged | 0.698 |
| | worsened | 0.826 |
| Backpropagation ANN | improved | 0.725 |
| | unchanged | 0.729 |
| | worsened | 0.819 |
| RNN | improved | 0.812 |
| | unchanged | 0.882 |
| | worsened | 0.856 |

TABLE 5

Testing results over the test set per classifier per visit.

| Algorithm | Classifier | v01 | v02 | v03 | v04 | v05 | v06 | v07 | v08 | v09 | Average ($F_1$) |
|---|---|---|---|---|---|---|---|---|---|---|---|
| SVM | improved | 0.4 | 0.42 | 0.42 | 0.42 | 0.48 | 0.5 | 0.5 | 0.49 | 0.5 | 0.458 |
| | unchanged | 0.5 | 0.5 | 0.51 | 0.51 | 0.55 | 0.55 | 0.56 | 0.55 | 0.55 | 0.531 |
| | worsened | 0.49 | 0.52 | 0.53 | 0.53 | 0.55 | 0.57 | 0.58 | 0.58 | 0.58 | 0.547 |
| RDF | improved | 0.58 | 0.56 | 0.59 | 0.59 | 0.59 | 0.62 | 0.62 | 0.62 | 0.63 | 0.6 |
| | unchanged | 0.64 | 0.68 | 0.68 | 0.68 | 0.71 | 0.69 | 0.67 | 0.67 | 0.67 | 0.676 |
| | worsened | 0.64 | 0.64 | 0.59 | 0.61 | 0.61 | 0.62 | 0.62 | 0.62 | 0.63 | 0.62 |
| Backpropagation ANN | improved | 0.4 | 0.55 | 0.55 | 0.55 | 0.71 | 0.73 | 0.73 | 0.77 | 0.77 | 0.64 |
| | unchanged | 0.5 | 0.69 | 0.72 | 0.76 | 0.75 | 0.75 | 0.79 | 0.82 | 0.86 | 0.737 |
| | worsened | 0.56 | 0.66 | 0.68 | 0.71 | 0.71 | 0.71 | 0.76 | 0.81 | 0.8 | 0.711 |
| RNN | improved | 0.61 | 0.65 | 0.73 | 0.73 | 0.75 | 0.84 | 0.85 | 0.83 | 0.79 | 0.753 |
| | unchanged | 0.76 | 0.79 | 0.85 | 0.85 | 0.86 | 0.85 | 0.87 | 0.87 | 0.87 | 0.841 |
| | worsened | 0.7 | 0.83 | 0.8 | 0.85 | 0.89 | 0.85 | 0.81 | 0.83 | 0.83 | 0.821 |

Combination of Models

In order to produce a complete prediction of the pain category progress for the OAI patients, a combination step of the classifiers was added corresponding to the three classes (improved, unchanged, and worsened). This is important because the three classifiers in each method are independent and only show one dimension (each) of the prediction result. The final combined prediction results per algorithm are shown in Table 6.

The description of the algorithm performing the combined predictions is as follows. For each of the 9 labels, the algorithm examines the outputs of each of the three classifiers and takes a weighted vote to determine whether a patient's pain level has been improved, unchanged, or worsened with respect to the previous reporting. There are 8 possible scenarios in play, with four distinct ones outlined below:

1. All three classifiers predict a positive class (that is, improved, unchanged, and worsened): the algorithm here chooses the classifier with the highest $F_1$-score as the prediction for that label.
2. All three classifiers predict a negative class (that is, not improved, not unchanged, and not worsened): the entire data point (i.e. the patient) is marked as a miss. The algorithm halts for that patient and does not compute any further predictions for the rest of the labels.
3. Two of the classifiers predict a negative class, while the other predicts a positive result. The classifier with the positive result is chosen to vote.
4. Two of the classifiers predict a positive class while a negative class is predicted by the third: in this case, the classifier with the highest $F_1$-score is chosen to vote. Here there are two subcases: first, if the classifier with the highest $F_1$-score predicts a positive class, its prediction is simply chosen; and second, if it predicts a negative class, the second best performing classifier is taken, which predicts a positive class.

TABLE 6

Testing results for combined classifiers per algorithm.

| Algorithm | $F_1$ |
|---|---|
| Baseline (MFC) | 0.413 |
| SVM | 0.502 |
| RDF | 0.612 |
| Backprop ANN | 0.686 |
| RNN | 0.811 |

Identifying pain trajectories and predicting pain improvement of OA patients automatically is of critical significance (both conceptual and practical) for understanding pain-related features, as well as the discovery and development of clinical medicine. Further, this development will aid in better-informed advice for a personalized treatment plan and on prognosis given by medical practitioners (trajectories). The examples focused on knee OA patients in the OAI dataset and demonstrated the feasibility of using ML to predict the pain improvement outcomes experienced by OA patients.

All ML models produced results higher than the baseline metric. Although the model was the worst performing in terms of the computation speed, the combined prediction results of the RNN classifiers proved to perform the best among the rest of the algorithms with an $F_1$-score of 0.815, followed by the backpropagation ANN model at 0.733 $F_1$.

This was also true for the individual single-class classifiers—the RNN classifiers outperformed all other models for the three pain classes discussed. The RNN model performed best due to its distinctive sequential characteristic, that is, it considers time as a factor in its prediction. Thus, it is important for ML applications to consider RNNs when faced with sequential or time-stamped data. The combined results are close to the averages reported by the individual classifiers within each algorithm. This explains why the second—and least desirable—case in the prediction combination algorithm did not occur often. The cross-validation shows an approximation of the results reported. Also, the cross-validation results indicate no model overfitting, which is a common problem with ML algorithms.

The classification results of individual labels show an up-trend for the classification performance over the 9 labels, where the first visit classification yielded a poorer performance compared with the next 8 labels. The RDF classifiers are an exception to this pattern, however. This may be due to its random nature in selecting an arbitrary set of features to build multiple decision trees, which repeats at every label producing a similar performance. The models are improving over time with labels due to the added feature of previous pain label. In fact, this feature was selected as the most significant feature by the RDF classifiers along with related injuries and the BMI values. Moreover, it is noticeable that the relative performance of the classifiers for each of the three classes was preserved across the four algorithms employed. The "unchanged" classifiers performed best, followed by the "worsened", and then "improved" ones. This is due to the distribution of patients in the OAI datasets, where more patients were reporting unchanged levels of pain than the improved and worsened ones. This further supports the characterization of OA as a disease of chronic symptoms rather than progressive ones.

The classifiers built were single-class models, which lead to an overhead exemplified in the prediction combination algorithm presented earlier. This can also result in missing data points entirely due to an ambiguous combined prediction (i.e., not improved, not unchanged, and not worsened). This can be solved by transforming the classifiers into multi-class classifiers, which will reduce the number of models needed to calculate to only a single classifier per ML method while increasing the amount of computation time and possibly reducing the performance per model due to the increased class space. In addition, the models presented only predict a single time step in the future (i.e., a 12-month period). This may be improved by identifying and extracting more discriminant features as well as performing a more extensive and complex hyperparameter optimization.

Embodiments of the subject invention capitalize on the performance of several ML algorithms to highlight the feasibility of automatic pain improvement prediction of OA patients. This direction can aid doctors, clinicians, medical students, and even researchers in disease and associated pain simulation and prediction.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

What is claimed is:

1. A method for predicting a pain level of an osteoarthritis (OA) patient, the method comprising:

developing, by a processor, a set of classifiers, the set of classifiers comprising three classifiers corresponding to a first category, a second category, and a third category, respectively;

training, by the processor, the set of classifiers;

testing, by the processor, the set of classifiers; and using, by the processor, the set of classifiers to predict the pain level of the OA patient at a future visit intended to assess the pain level, the first category being that pain has improved for the OA patient since a previous visit, the second category being that pain has remained unchanged for the OA patient since the previous visit, and the third category being that pain has worsened for the OA patient since the previous visit, the developing, training, testing, and using of the set of classifiers comprising using a machine learning (ML) technique that factors in sex, age, body mass index, injury factors, occupation factors, medical history, strength performance measures, and physical activity factors for the OA patient, the developing of the set of classifiers comprising feature selection, the feature selection comprising utilizing a Fisher coefficient and a squared Euclidean distance on features of the set of classifiers, the ML technique being a recurrent neural network (RNN) with three single class, multi-label RNN classifiers, the training of the set of classifiers comprising training the set of classifiers using a dataset with known values, the testing of the set of classifiers comprising testing the set of classifiers using the dataset with known values, the dataset being broken into a first sub-dataset to be used for the training of the set of classifiers and a second sub-dataset to be used for the testing of the set of classifiers, the training of the set of classifiers comprising normalization of data obtained from the dataset, the using of the set of classifiers to predict the pain level of the OA patient comprising using the set of classifiers to predict the pain level of the OA patient at an Nth visit based on features of the set of classifiers reported on all visits up to an (N−1)th visit, the training of the set of classifiers comprising rescaling the age and body mass index for the OA patient to a unified range from 0 to 1, the feature selection comprising decomposing first features, of the features of the set of classifiers, into independent constituents and aggregating second features, of the features of the set of classifiers, into an aggregated group of features, and the feature selection further comprising binarizing all of the features of the set of classifiers using a binary threshold function where a feature value of 1 is assigned to a respective feature if it is higher than a threshold of the binary threshold function and a feature value of 0 is assigned to the respective feature if it is lower than the threshold of the binary threshold function.

2. The method according to claim 1, the dataset with known values being the Osteoarthritis Initiative (OAI) dataset.

3. The method according to claim 1, the using of the set of classifiers comprising choosing a classifier from the set of classifiers to predict the pain level of the OA patient, where, if all classifiers of the set of classifiers predict a positive class, the chosen classifier is that with a highest F1-score, where, if only one classifier of the set of classifiers predicts a positive class, the chosen classifier is the classifier that predicts a positive result, and where, if more than one classifier, but less than all classifiers, of the set of classifiers predicts a positive class, the chosen classifier is the classifier that with a highest F1-score that also predicts a positive result.

4. A system for predicting a pain level of an osteoarthritis (OA) patient, the system comprising:

a processor; and a machine-readable medium in operable communication with the processor and having instructions stored thereon that, when executed by the processor, perform the following steps:

developing a set of classifiers, the set of classifiers comprising three classifiers corresponding to a first category, a second category, and a third category, respectively;

training the set of classifiers;

testing the set of classifiers; and using the set of classifiers to predict the pain level of the OA patient at a future visit intended to assess the pain level, the first category being that pain has improved for the OA patient since a previous visit, the second category being that pain has remained unchanged for the OA patient since the previous visit, and the third category being that pain has worsened for the OA patient since the previous visit, the developing, training, testing, and using of the set of classifiers comprising using a machine learning (ML) technique that factors in sex, age, body mass index, injury factors, occupation factors, medical history, strength performance measures, and physical activity factors for the OA patient, the ML technique being an RNN with three single class, multi-label RNN classifiers, the training of the set of classifiers comprising training the set of classifiers using a dataset with known values, the testing of the set of classifiers comprising testing the set of classifiers using the dataset with known values, the dataset being broken into a first sub-dataset to be used for the training of the set of classifiers and a second sub-dataset to be used for the testing of the set of classifiers, the developing of the set of classifiers comprising feature selection, the training of the set of classifiers comprising normalization of data obtained from the dataset, the using of the set of classifiers to predict the pain level of the OA patient comprising using the set of classifiers to predict the pain level of the OA patient at an Nth visit based on features of the set of classifiers reported on all visits up to an (N−1)th visit, the feature selection comprising utilizing a Fisher coefficient and a squared Euclidean distance on the features of the set of classifiers, the training of the set of classifiers comprising rescaling the age and body mass index for the OA patient to a unified range from 0 to 1, the feature selection comprising decomposing first features, of the features of the set of classifiers, into independent constituents and aggregating second features, of the features of the set of classifiers, into an aggregated group of features, and the feature selection further comprising binarizing all of the features of the set of classifiers using a binary threshold function where a feature value of 1 is assigned to a respective feature if it is higher than a threshold of the binary threshold function and a feature value of 0 is assigned to the respective feature if it is lower than the threshold of the binary threshold function.

5. The system according to claim 4, the using of the set of classifiers comprising choosing a classifier from the set of classifiers to predict the pain level of the OA patient, where, if all classifiers of the set of classifiers predict a positive class, the chosen classifier is that with a highest F1-score, where, if only one classifier of the set of classifiers predicts a positive class, the chosen classifier is the classifier that predicts a positive result, and where, if more than one classifier, but less than all classifiers, of the set of classifiers predicts a positive class, the chosen classifier is the classifier that with a highest F1-score that also predicts a positive result.

* * * * *